United States Patent [19]

Hook et al.

[11] Patent Number: 4,983,164
[45] Date of Patent: Jan. 8, 1991

[54] AUTOMATIC TWO-CHAMBER INJECTOR

[75] Inventors: Karl-Axel Hook, Eskilstuna; Nils B. Nilson, Mjolby; Kjell I. Wellenstam, Gothenburg, all of Sweden

[73] Assignee: Astra Meditec AB, Molndal, Sweden

[21] Appl. No.: 180,455

[22] Filed: Apr. 12, 1988

[30] Foreign Application Priority Data

Apr. 14, 1987 [SE] Sweden .................................. 8701548

[51] Int. Cl.$^5$ .............................................. A61M 37/00
[52] U.S. Cl. ......................................... 604/87; 604/56; 604/139
[58] Field of Search .............................. 604/56, 87–90, 604/136–139, 191

[56] References Cited

U.S. PATENT DOCUMENTS

| 1,943,120 | 1/1934 | Kabnick ................. 604/87 |
| 2,708,438 | 5/1955 | Cohen .................... 604/87 |
| 2,778,360 | 1/1957 | Miskel .................... 604/87 |
| 3,136,313 | 6/1964 | Enstrom et al. ....... 604/137 |
| 3,340,873 | 9/1967 | Solowey ................ 604/87 |
| 3,537,605 | 11/1970 | Solowey ............. 604/87 X |
| 4,055,177 | 10/1977 | Cohen ................ 604/90 X |
| 4,059,109 | 11/1977 | Tischlinger ......... 604/90 X |
| 4,202,314 | 5/1980 | Smirnov et al. ...... 604/138 |
| 4,214,584 | 7/1980 | Smirnov et al. ...... 604/138 |
| 4,413,991 | 11/1983 | Schmitz et al. ...... 604/191 |
| 4,529,403 | 7/1985 | Kamstra ............... 604/136 |
| 4,648,532 | 3/1987 | Green ................. 604/87 X |

Primary Examiner—Stephen C. Pellegrino
Assistant Examiner—C. Maglione
Attorney, Agent, or Firm—White & Case

[57] ABSTRACT

The invention relates to an automatic two-chamber injector for mixing and injecting a medical solution. The injector comprises a barrel (11) having a first end with a receiving portion (15) for an injection needle (17), said portion being sealed prior to use, and a second end with a displaceable plunger (27). The barrel (11) comprises two chambers (29, 30) separated by a migrationproof membrane (28), said membrane (28) being adapted to rupture when the plunger (27) is displaced towards the first end of the barrel (11).

The invention also related to a method for mixing and injecting a solution by means of an automatic two-chamber injector and to a cartridge for a two-chamber injector.

30 Claims, 6 Drawing Sheets

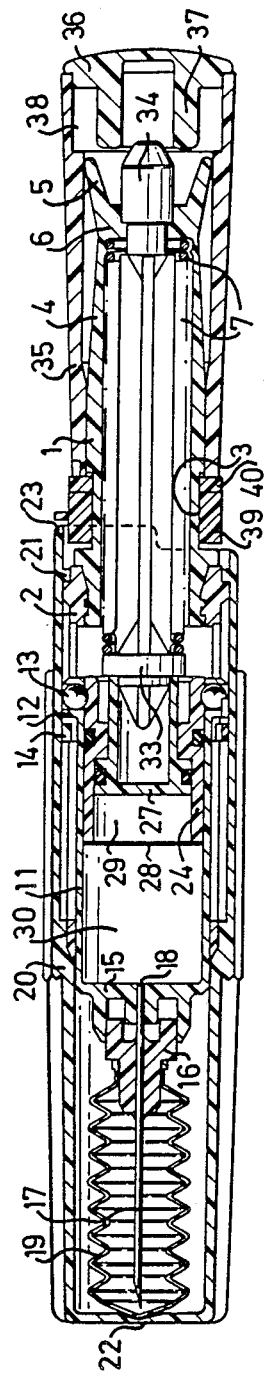
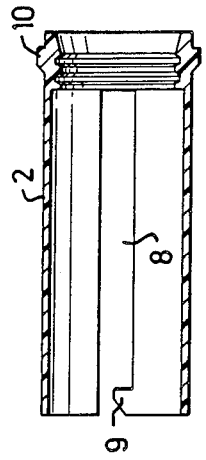
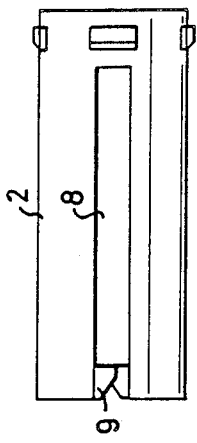
FIG. 1
FIG. 2A
FIG. 2B

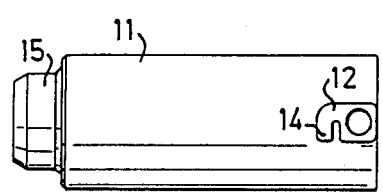
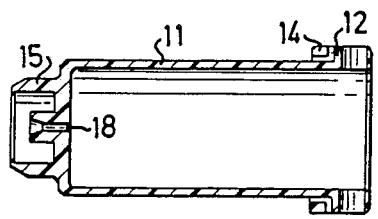
FIG.3A    FIG.3B
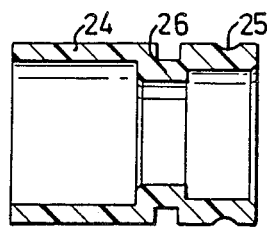
FIG.4
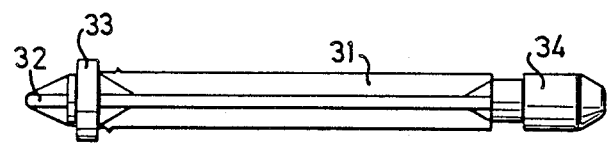
FIG.5

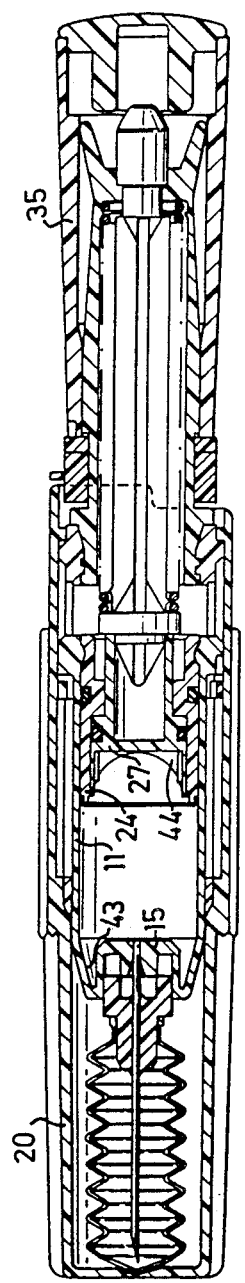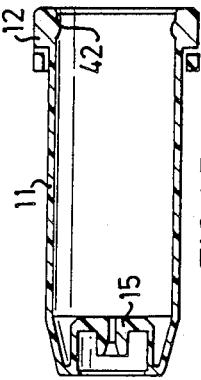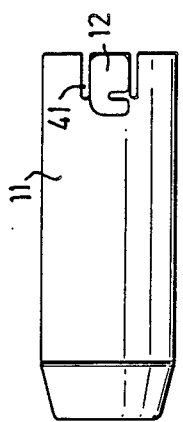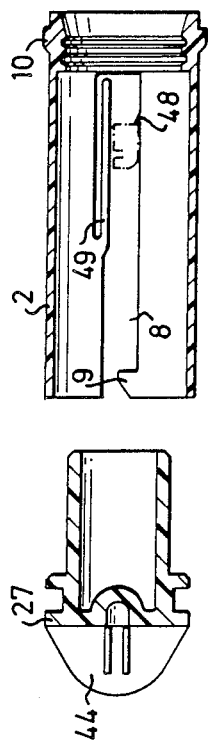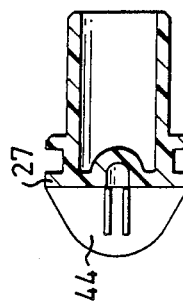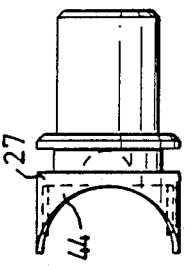

AUTOMATIC TWO-CHAMBER INJECTOR

FIELD OF THE INVENTION

The invention relates to an automatic two-chamber injector comprising a barrel having a front end with a receiving portion for an injection needle and a rear end provided with a slidable plunger, said receiving portion being sealed prior to use.

The invention also relates to a method for mixing and injecting a solution by means of an automatic two-chamber injector and to a cartridge for a two-chamber injector.

BACKGROUND OF THE INVENTION

Automatic injectors have been developed specially for use by persons who for some reason must inject a solution into their own body at a time which cannot be predicted, e.g. soldiers who have been subjected to nerve gas in war. These injectors are stored for years and are further more often subjected to hard conditions during the time the potential user carries it, which sometimes may be long. When the automatic injector finally is to be used it must work with a great reliability when an injection is to be carried out. At such a critical moment it is important that the injector can be handled and activated in a simple and quick manner. Consequently, there are special requirements on automatic injectors of the type mentioned above regarding reliability and simplicity in both handling and operation.

Lately effective antidotes against nerve gases have been developed, said antidotes being stable in the form of a powder, but having proved difficult to make stable in solution, especially during the long storage periods being normal in this field of application. Consequently there is a demand for automatic injectors which are simple, quick and reliable and in which it is possible to store two substances separately for a long period and wherein said substances also easily can be mixed before use.

Some different types of automatic two chamber injectors are previously known:

U.S. Pat. No. 4,529,403 discloses an automatic two-chamber injector with an ampoule located between the injection needle and the plunger. The ampoule is provided with one or several pistons of flexible material, as rubber, keeping the injection solutions separated from each other. In the front part of the ampoule there are sidewardly arranged channels or sections, which permit the injection solutions to pass the piston or pistons.

U.S. Pat. No. 4,413,991 discloses another system for an automatic two chamber injector, in which a plunger drives an injection needle through two separate chambers containing different solutions. The injection needle is provided with side-openings interconnecting the two chambers during injection.

U.S. Pat. No. 4,202,314 discloses a system with two chambers whose contents are mixed and then automatically injected. Two driving systems are arranged, one for mixing and the other for injection. The injection needle is located inside the cartridge.

In the embodiment disclosed in U.S. Pat. No. 4,214,584, separate chambers are concentrically arranged with and separated by a cylindrical wall from a first chamber. In order to mix the contents of the chambers, the cylindrical wall is screwed upwards by which means the chambers are united with the first chamber. In this embodiment as well, the injection needle is arranged inside the cartridge prior to use.

The previously known automatic two chamber injectors have a number of disadvantages:

The use of polymer material to separate a solution from a powder, alternatively a solution from a solution, has the consequence that a permeation of liquid to some extent is inevitable during a long storage period.

The mixing of the separated medical substances is incomplete and may in some cases be non-existent.

To mount the injection needle inside the cartridge in an injection solution involves a great risk that the injection needle will be corroded during a long storage period.

If a complicated operation to achieve a sufficient mixture of the substances has to be carried out, in conjunction with a lack of a precise control of the operation, there is a risk that the injector may be used in a erroneous way, causing non-appearance of medical effects and even risks for accidents.

There is no possibility to replace the cartridge whilst preserving the sterile conditions.

SUMMARY OF THE INVENTION

The object of the present invention is to solve the above problems by providing an automatic two-chamber injector having a cartridge, in which the two substances are separated in a way that permits safe and long storage and where a complete mixing of the substances will be achieved. The operation of the injector is quick and simple and, due to the construction of the injector, it is impossible to use the injector wrongly.

In particular, the invention can be used for mixing two or several medical substances immediately before use, one of the substances being a liquid and the other/others being in powder or liquid form, and for a subsequent injection of the mixed solution. The device makes it possible to store medical preparations separately and under sterile conditions, to mix the preparations immediately before injection and to inject the fresh and completely mixed solution into the body tissue.

An automatic two-chamber injector as described by way of introduction and in accordance with the invention is characterized in that the barrel comprises two chambers separated by a migration proof membrane, said membrane being adapted to rupture when the plunger is displaced towards the front end of the barrel.

Other advantageous features of the invention will become apparant from the following description of embodiments of the invention and from the dependent claims.

According to the invention the advantage is obtained that the membrane, which separates the two chamber from each other, prevents liquid migration and this fact results in an increased durability for the contents of the cartridge. Furthermore, the position of the injection needle outside the barrel itself, without any contact with the injection solution, contributes to an increased durability since the risk of corrosion is avoided.

By the design of the front cover and its interaction with the barrel, the operation of the device is sequentially completely controlled with a complete mixing and a subsequent activation and injection. The construction of the device only permits an operation in predetermined steps following each other, which results in a simple and, above all, a safe function. A fine motoric action by means of a hand movement is required to operate the front cover rotatingly. This is an additional safety aspect since an unintentional actuation is impossible, for instance due to influences in the form of for example thrusts or pressure or due to that a part gets caught in an adjacent object.

The rotatable front cover is designed in such a way as to be rotatable in one direction only, which means there is a possibility of control if the injector has been activated prematurely and if the mixing phase has been activated long before the injector is to be used.

The two-chamber injector according to the invention is manufactured of simple materials and is simple in its construction which means that it is well suited for use as a disposable injector. The barrel with the injection needle together forms a separate, detachable unit which gives additional fields of application and additional advantages. After an injection the front cover can be dismounted and the used cartridge can be exchanged for a new one. The driving unit is re-loaded and the front cover is mounted, whereafter the injector is ready for use again. Since the cartridge with its contents often may have a shorter durability than the mechanical unit, it is a great advantage to be able to store the cartridge separately at a prolonged storage, e.g. for military use. If tne stored injectors have not been used during their life span, the cartridge can be exchanged and replaced by a new one, which situation should be compared with a situation where the entire two-chamber injector must be replaced. This system also gives a possibility to choose between different medical substances in alternative cartridges which means there is a possibility of adaptation to different expected situations.

The two-chamber injector according to the invention is mainly intended for military purposes, but it is also suitable for use in other human medical disciplines as well as in veterinary medicine.

BRIEF DESCRIPTION OF THE DRAWINGS

An embodiment of an automatic two-chamber injector according to the invention and modifications thereof will be described in detail below in connection with the accompanying drawings, where FIG. 1 shows a longitudinal sectional view through a first embodiment of the two-chamber injector prior to use, FIG. 2a–b show a side elevation view and a longitudinal sectional view of the guide sleeve according to FIG. 1, FIG. 3a–b show a side elevation view and a longitudinal sectional view of the barrel according to FIG. 1, FIG. 4 shows the powder-chamber, somewhat enlarged, FIG. 5 shows a side elevation view of the spring carrier, FIG. 7 shows a longitudinal sectional view of a second embodiment of the two-chamber injector prior to use, FIG. 8 shows a longitudinal sectional view of a second embodiment of the guide sleeve, FIG. 9a–b show a side elevation view and a longitudinal sectional view of the barrel according to FIG. 7, FIG. 10a–b show a side elevation view and a longitudinal sectional view of the plunger according to FIG. 7, FIG. 11a–d show parts of the two chamber injector according to FIG. 1 during different phases of actuation, where

DETAILED DESCRIPTION OF PREFERRED EMBODIMENTS OF THE INVENTION

Figure 6A:
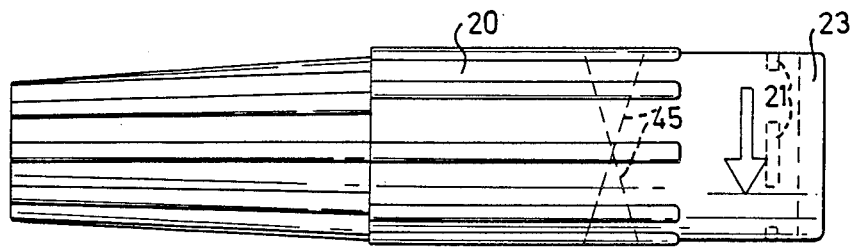
FIG. 6a–b show a side elevation view and a longitudinal sectional view of the front cover.

The embodiment of the two-chamber injector shown in FIGS. 1–6 comprises a body which consists of a locking sleeve (1) and a guide sleeve (2), which is attached onto the locking sleeve (1) by means of threads. The locking sleeve (1) comprises an annular groove (3) and is further split into a number of resilient longitudinal arms (4), preferably four, which at their free ends form diverging tongues (5). Interior of the free ends of the arms (4) radial flange portions (6) are provided which form a seat for a spring (7) mounted inside the locking sleeve (1). The guide sleeve (2), shown in FIG. 2a–b, comprises two diametrically opposed running grooves (8) extending outside the area of the threaded part, said running grooves ending with stop lugs (9). The other end of the sleeve is provided with a number of external pins (10). A barrel (11), shown in FIG. 3a–b, is slidably displaceable in the guide sleeve (2) by means of two sliding lugs (12) which are positioned externally and diametrically opposed on the barrel and run in the running grooves (8) of the guide sleeve. A sliding lug (12) comprises a through hole for the enclosure of a ball (13) and comprises further a resilient tongue (14). The barrel (11) is sealed at a front end to form a receiving portion (15) in which a needle holder (16) with a hollow injection needle (17) is slidably displaceable. The receiving portion (15) has a centrally placed aperture into which the rear part of the injection needle (17) is inserted and in whose bottom a piercable membrane (18) is arranged. The front part of the injection needle (17) is enclosed by a protective bellows (19) in order to keep the injection needle sterile.

Figure 6B:
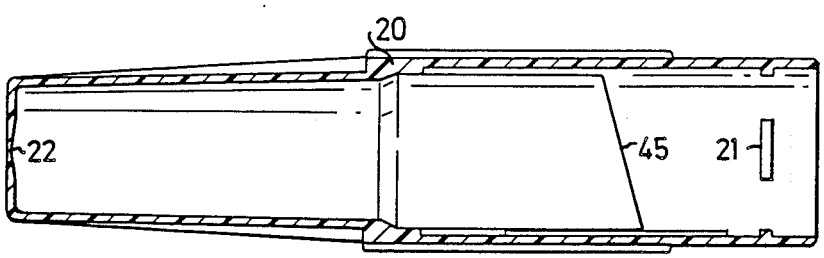

The barrel (11) with the injection needle (17) and the guide sleeve (2) are surrounded by a front cover (20) which is rotatable on the guide sleeve (2) and which is shown in FIG. 6a–b. The front cover is provided with external ribs in order to ensure a safe grip on the cover. A number of internal locking lugs (21) are adapted for interaction with the pins (10) of the guide sleeve. The front cover is closed at its front end, said front end having a central part (22) formed with a wall thickness which is considerably thinner than the wall thickness of the other parts. At the rear end of the front cover a prolonged part (23) is formed on about half the circumference of the cover. The part of the front cover which surrounds the guide sleeve (2) has two internal slideways (45) being displaced 180° in relation to each other and being arranged for interaction with the sliding lugs (12) of the barrel. A number of additional grooves are arranged in this part of the front cover, which will be described in detail below.

Inside the barrel (11), at the end opposite to the receiving portion, a powder chamber (24) according to FIG. 4 is arranged. The envelope surface of the powder chamber is provided with a circumferential external groove (25) to receive the ball (13) of the sliding lug of the barrel. An additional annular groove is arranged for a sealing. An internal bead (26) forms a seat for a plunger (27) being displaceable in the powder chamber (24) to a limited extent, said plunger being provided with a sealing against the inner surface of the powder chamber at one end. An aluminum-membrane (28) with a plastic coating is welded at the inner end of the powder chamber (24) and defines a chamber (29) together with the plunger (27) for one of the substances. In the barrel (11), a second chamber (30) is formed on the other side of the aluminum-membrane (28), said second chamber containing the second substance.

The plunger (27) bears, with its non-sealed, open end, on a contact ring (33) on a spring carrier (31), also shown in FIG. 5. The spring carrier comprises a cone-shaped centering portion (32) located on the front end and being arranged on the contact ring, said portion being inserted into the open end of the plunger. The rear end of the spring carrier has a locking head (34) and a flanged middle part extends between the two ends. The locking head (34) interacts with locking lugs in the flange parts (6) on the arms of the locking sleeve for a compression of the spring (7) being arranged around the spring carrier (31) between the flange parts (6) and the contact ring (33).

The locking sleeve (1) is surrounded by a displaceable rearward cover (35), said rearward cover extending up to the edge of the annular groove (3) of the locking sleeve. The opposite end of the rearward cover is closed by an activating knob (36) having a cylindrical guiding flange (37) which extends into the rearward cover. The rearward cover is widened internally in the area of the cylindrical guiding flange (37) in order to form a circumferential internal guiding channel (38) at the extreme end of the rearward cover.

A resilient safety ring (39) is arranged in the cylindrical groove (3) of the locking sleeve between the rearward cover (35) and the front cover (20), said ring having a circumferential extent of about 220°. A thin ring (40) is arranged in the groove (3) alongside the safety ring (39), said ring (40) and said safety ring (39) being interconnected by means of a loose loop (not shown), the purpose being to keep the safety ring with the injector even after it has been detached from the groove.

FIGS. 7-10 show a second embodiment of a two-chamber injector, which differs from the embodiment according to FIGS. 1-6 only by an alternative embodiment of the guide sleeve (2), the barrel (11) and the plunger (27). The guide sleeve (2), shown in FIG. 8, differs from the embodiment in FIG. 2 only by an alternative embodiment of the running groove 8. In order to prevent an unintentional displacement of the barrel (11) and the powder chamber (24) towards the plunger (27) and thereby causing a premature mixing process, the running groove (8) is provided with a second stop lug (48) which interacts with the sliding lug (12) to stop said sliding lug (12) against further displacement in a position of the sliding lug which corresponds to the starting point of the oblique slide-way. A resilient tongue (49) is arranged along one longitudinal side of the running groove (8) opposite to the stop lug (48). When the mixing phase is due the oblique slide-way (45) presses against the rounded edges of the sliding lug (12) with a force that presses the resilient tongue (49) outwards, allowing the sliding lug (12) to pass the stop lug (48) and the mixing takes place. On each side of the two sliding lugs (12) of the barrel there are slits (41) (see FIG. 9a-b) in order to permit the respective sliding lug (12) to move resiliently. Spherical knobs (42) are arranged on the inner surfaces of the lug for interaction with the circumferential grooves (25) of the powder chamber (24). Furthermore, the front part of the barrel is provided with a circumferential cylindrical channel (43) surrounding the receiving portion (15). The plunger (27), shown in FIG. 10a-b, is provided with one or several piercing means (44), which are inserted in the cylindrical channel (43) of the barrel (11) surrounding the receiving portion when the plunger (27) is in its extended position. The piercing means (44) are arranged on the plunger to mechanically rupture the membrane (28) when the barrel and powder chamber is displaced towards the plunger.

The operation of the two chamber injector comprises two steps, one mixing step and one releasing and injecting step. These steps will be described below in detail with reference to FIG. 11a-d showing parts of the two-chamber injector in different phases.

FIG. 11 a shows the injector in its initial position in which position it contains a liquid in one chamber (30) separated from a powder in the second chamber (29) by an aluminum-membrane (28). In the initial position the prolonged part (23) of the front cover covers the safety ring (39) in a way that makes it impossible to release the safety ring prematurely. In order to mix the two substances the front cover (20) is rotated, whereby the sliding lugs (12) slide on the oblique slide-ways (45), thus being pressed rearwards in the running grooves (8). The balls (13)/the lugs (12) are pressed against the circumferential grooves (25) of the powder chamber by the inner surface of the front cover (20), which results in that both the barrel (11) and the powder chamber (24) are displaced backwards together with the sliding lugs (12). The powder chamber is thereby displaced towards the plunger (27), whereby the pressure in the chamber (29) increases and the aluminum-membrane (28) ruptures, alternatively the piercing means rupture the aluminum-membrane (28).

Figure 11A:
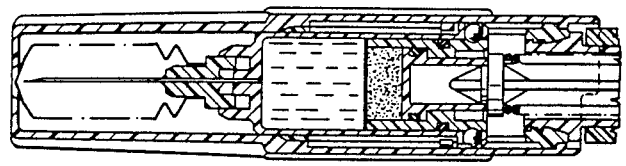
FIG. 11a shows the starting phase.
Figure 11B:
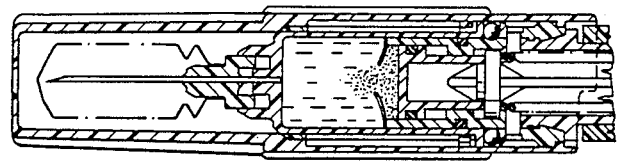
FIG. 11b shows the mixing phase.

FIG. 11b shows a position where the aluminum-membrane has been ruptured and the powder is pressed out of its chamber (29) to be mixed with the liquid. When the sliding lug (12) reaches the end of the oblique slide-way (45) the whole cartridge (11, 16, 17) and the powder chamber (24) are moved back to a position where the end surfaces of the plunger (27) and the powder chamber (24) are located in one common plane and the contact ring (33) of the spring carrier bears on the internal bead (26) of the powder chamber. The mixing phase is now completed but it can be complemented, if necessary, by an agitation of the injector.

After the mixing phase the front cover is in such a relative position of rotation that the prolonged part in the outer end covers the opening of the safety ring (39) at the same time as the sliding lugs (12) are located in longitudinal grooves D,D' (see FIG. 13) in the front cover, said grooves permitting the balls (13)/the spherical knobs (42) to be freed from the circumferential grooves (25) of the powder chamber. The two-chamber injector is now ready for a triggering and injection phase which is started by disengaging the safety ring (39) from the cylindrical groove (3) of the locking sleeve after which the injector is placed against the part of the body into which the injection is to take place.

Figure 12:
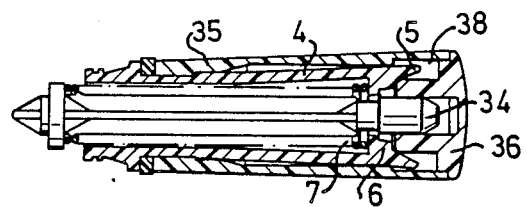
FIG. 12 shows a longitudinal sectional view of the rearward cover in a position when the spring is released.

The activating knob (36) and the rearward cover (35) are pressed and displaced towards the front cover. This is now possible since the safety ring (39) is disengaged. The displacement of the rearward cover relative to the backing sleeve will achieve a release of the spring (7) in a way shown in FIG. 12. The diverging tongues (5) of the locking sleeve are guided into the guiding channel (38), whereby the flange parts of the resilient arms diverge and the locking head (34) of the spring carrier, as well as the spring (7), are released.

Figure 11C:
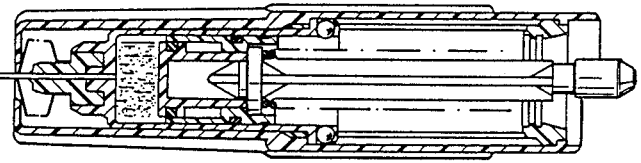
FIG. 11c shows the injection phase and FIG. 11c shows the phase of completed injection.

FIG. 11c shows the two-chamber injector in a position in which the injection has started. The spring (7) presses the powder chamber (24) and the plunger (27) forward together. Since the balls (13)/the lugs (12) now can be forced up into the grooves in the front cover, the powder chamber is released from the barrel (11). The plunger presses against the liquid which transmits the pressure hydraulically to the barrel which is driven forwards, by which means the injection needle (17) penetrates the thin material in the central part (22) of the front cover. When the protection bellows (19) is compressed, the needle holder (16) is pushed into the receiving portion (15) and the rear point of the injection needle (17) penetrates the membrane (18). In this position a connection between the mixed solution and the injection needle is obtained and the injection starts and continues during the common forward movement of the powder chamber (24) and the plunger (27).

Figure 11D:
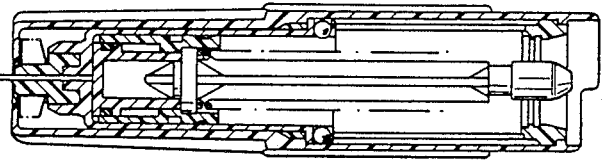

FIG. 11d shows the position when the injection is finished and the barrel (11), the powder chamber (24) and the plunger (27) all have been displaced to their respective end positions under the influence of the spring and all the mixed solution have been injected into the patient.

Figure 13:
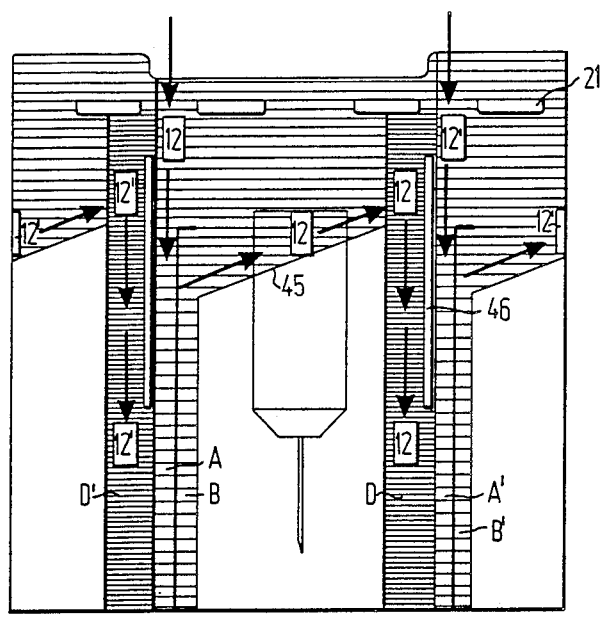
FIG. 13 is a schematic view showing the inner surface of the front cover with the cover slit and unfolded in the plane of the paper.

FIG. 13 is a schematic view showing the inner surface of the front cover (20) and the way of the sliding lugs (12, 12') along said inner surface when the front cover is rotated. When the front cover is mounted, it is guided over the guide sleeve in such a way that the sliding lug (12) (corresponding to the second lug 12' with 180° displacement) is moved along the groove A and the locking lugs (21) passes between the pins (10). All grooves are formed with a sharp edge in "the direction of non-rotation" for interaction with the resilent tongue (14) of the sliding lugs which falls in behind the sharp edge and thereby prevents a rotation of the front cover (20) in the wrong direction. Subsequently, the front cover is rotated one step further until the sliding lug (12) reaches groove B. Groove B constitutes the starting position for the operation of the two-chamber injector. If the front cover is rotated, the sliding lug (12) is moved along the oblique slide-way (45) and the rotation movement is stopped when the sliding lug (12) meets the internal edge (46). The sliding lug is now positioned in a groove D which is the groove wherein the sliding lug (12) is located in the releasing and injection phase, said groove having a depth which will allow the ball (13)/the spherical knob (42) to be released from the circumferential groove (25) of the powder chamber. During the injection phase the sliding lug (12) moves along the groove D where it will reach its final position if the two-chamber injector is not to be re-used. For the dismounting of the front cover, the cover is rotated one further step whereby the sliding lug passes below the edge (46) and into the groove A', being displaced 180° in relation to groove A. In this position the front cover can be dismounted from the guide sleeve since the locking lugs will be free from the pins (10).

The invention is in no way limited to the embodiments described above and several possible modifications of the invention are possible within the scope of the claims. For example, the membrane, which separates the chambers from each other, can be made of other migrationproof materials. The number and the design of the perforating means for the mechanical rupture of the membrane can also be varied.

We claim:

1. An automatic two-chamber injector comprising:
   a barrel having a forward end with a receiving portion for an injection needle and a second end;
   seal means for sealing the forward end of the barrel;
   a slidable plunger disposed in the second end of the barrel;
   a needle assembly received in said receiving portion and displaceable from a first position to a second position for puncturing the seal means;
   a migration proof membrane disposed in said barrel for separating the barrel into two chambers, the membrane being rupturable;
   first actuating means for moving said plunger and said membrane toward one another for causing said membrane to rupture while said needle assembly is in said first position; and
   second actuating means for causing said needle assembly to move to the second position, and for discharging the contents of said chamber through said needle assembly; such that the contents of the two chambers are mixed prior to breaking the seal means;
   wherein said first actuating means comprises a front cover rotatably disposed about said barrel, and wherein said front cover includes guide means for moving said membrane relative to said plunger responsive to rotation of said cover from one rotational position to another.

2. An automatic two-chamber injection as defined in claim 1, comprising means to prevent actuation of said second actuating means until after actuation of said first actuating means.

3. An automatic two-chamber injector as defined in claim 1, wherein said guide means selectively engages at least one guide member on said barrel for moving said barrel and membrane responsive to rotation of said cover.

4. An automatic two-chamber injection as defined in claim 1, comprising a powder chamber slidingly arranged in the second end of the barrel and defining one of the two said chambers, wherein said membrane is disposed on said powder chamber, and wherein said powder chamber has means for selectively engaging said guide means for moving towards said plunger responsive to rotation of said cover for rupturing the membrane.

5. An automatic two-chamber injector as defined in claim 4, wherein said guide means selectively engages at least one guide member of said barrel, which guide member in turn selectively engages the engagement means on said power chamber, for moving said barrel and powder chamber towards said plunger.

6. An automatic two-chamber injection as defined in claim 5, wherein said guide means includes means for permitting said guide member to move out of engagement with said powder chamber after retraction such that said powder chamber is free thereafter to be moved forward in said barrel by said second actuating means.

7. An automatic two-chamber injector as defined in claims 3, 4, 5 or 6, comprising actuatable biasing means for urging said plunger to move forward for discharging the contents of said chambers, and release means for selectively actuating said biasing means.

8. An automatic two-chamber injector as defined in claim 7, wherein the cover has a closed front end over said needle assembly, and the guide means in said cover include means, in one rotational position of the cover, to allow said barrel and needle assembly, upon actuation of said biasing means, to move forward in said cover and the needle to puncture said front end of the cover.

9. An automatic two-chamber injector as defined in claim 8, wherein said receiving portion is constructed such that the force of impact of the needle against the cover causes the needle assembly to retract into the second position and penetrate the seal means.

10. An automatic two-chamber injector as defined in claim 9, wherein the biasing means comprises a spring carrier having a forward end engaging the plunger and a locking head at its other end, a locking sleeve having a flange portion which is movable into and out of engagement with the locking head for selectively locking the spring carrier against axial movement; a spring engaging the forward end of the spring carrier for urging the spring carrier toward the powder chamber; and wherein the release means comprises means for selectively moving the flange portion out of engagement with the locking head for releasing the spring carrier.

11. An automatic two-chamber injector as defined in claim 10, comprising lock means for preventing the actuation of the release means until after the contents of the two chambers having been mixed and the barrel is rotatably in position to move forward inside the cover.

12. An automatic two-chamber injector comprising:
a housing having an axis;
a barrel axially displaceable in said housing, and having a forward end, with a receiving portion for an injection needle, and a second end;
a slidable plunger disposed in the second end of the barrel;
a needle received in said receiving portion;
a migration proof membrane disposed in said barrel for separating the barrel into two chambers, the membrane being rupturable;
means cooperating with said housing for holding said plunger against axial movement away from said barrel;
first actuation means for moving said membrane toward said plunger for rupturing the membrane; and
second actuation means for urging said plunger toward the forward end of the barrel for discharging the contents of the chambers through the needle.

13. An automatic two-chamber injector according to claim 12, wherein the first actuation means comprises a sleeve rotatable about the barrel and having guide means for moving said membrane toward said plunger responsive to rotation of the sleeve between first and second rotational positions.

14. An automatic two-chamber injector according to claim 13, wherein said guide means engage at least one guide member on said barrel for moving said barrel and membrane toward said plunger.

15. An automatic two-chamber injector according to claim 13, comprising a powder chamber slidingly arranged in the barrel and defining one of the two chambers; wherein said membrane is disposed on said powder chamber, and wherein said powder chamber has means for selectively engaging said guide means for moving towards said plunger response to rotation of said sleeve for rupturing the membrane.

16. An automatic two-chamber injector according to claim 15, wherein at one rotational position of said sleeve said powder chamber is free to move forward in said barrel.

17. An automatic two-chamber injector according to claim 16, wherein said powder chamber is disposed in the second end of the barrel; wherein said guide means engage at least one guide member on said barrel, which guide member in turn selectively engages the engagement means of said powder chamber, for moving said barrel and powder chamber toward said plunger, and wherein said guide means, at the said one rotational position of said sleeve, permits the guide member to move out of engagement with the powder chamber and permits said barrel to move forward in said housing and said powder chamber to move forward in said barrel.

18. An automatic two-chamber injector according to claim 13, wherein said second actuation means comprises spring-loaded drive mean for urging said plunger toward the forward end of the barrel, and release means for releasing the spring-loaded drive means.

19. An automatic two-chamber injector according to claim 18, wherein the second actuating means comprises a safety means for preventing premature actuation of said release means.

20. An automatic two-chamber injector according to claim 19, wherein said guide means comprises oblique sideways arranged on the inner surface of the sleeve, and wherein said at least one guide member comprises sliding lugs on the barrel, so as to displace the barrel when the front cover is rotated.

21. An automatic two-chamber injector according to claim 20, wherein the powder chamber is displaceable in the barrel in one rotational position of the sleeve and is locked in the barrel in other rotational positions of the sleeve.

22. An automatic two-chamber injector according to claim 21, wherein each sliding lug comprises a knob arranged for interaction with a groove in the powder chamber, to lock said powder chamber in the barrel.

23. An automatic two-chamber injector according to claim 21, wherein at least one axial groove is arranged in the inner surface of the sleeve to accommodate parts of a respective sliding lug in one of the rotational positions of the front cover in order to allow the powder chamber to disengage from the barrel.

24. An automatic two-chamber injector according to claim 23, wherein the injection needle is displaceable in the receiving portion and is sterilely surrounded by a protective bellows prior to use, said receiving portion being sealed from the barrel by means of a seal which is penetrated when said injection needle is displaced in said receiving portion.

25. An automatic two-chamber injector according to claim 24 wherein the barrel with the powder chamber and the plunger forms a replaceable unit together with the injection needle which is surrounded by the protective bellows.

26. An automatic two-chamber injector according to claim 25, wherein said sleeve is in the form of a front cover closed at one end and having an opposite open end, wherein the front cover includes a pair of first axial guide portions extending from the open end for receiving the lugs of the barrel and for guiding the lugs to a position adjacent one side of the oblique slideways, wherein said axial grooves are adjacent the opposite ends of the slideways; wherein each said axial groove has a forward end; wherein the cover includes a pair of second axial guide portions communicating with the respective axial grooves, wherein each of the second axial guide portions extends to the open end of the cover; and comprising means for locking said cover onto said barrel while said lugs are rotationally in said slideways and said axial grooves; whereby the front cover can be inserted over the barrel, with the lugs moving down said first guide portion, and rotated into locking position, such that the cover is locked on the barrel; and whereby after actuation, in which the lugs have been rotated along the slideways and pushed forward in the first grooves, the cover may be rotated to move the lugs into the second guide portions to permit removal of the cover and replacement of the barrel unit.

27. An automatic two-chamber injector according to claim 25, wherein one or more piercing means are arranged on the plunger in order to pierce the membrane, said piercing means being accommodated in an interior cylindrical channel at said first end of the barrel when said plunger is positioned in its most protruding position.

28. A method of storing, mixing, and injecting a solution by means of an automatic two-chamber injector, comprising the steps of:

provinding a barrel having a forward end, with a receiving portion for receiving an injection needle and permitting axial movement of the needle towards the barrel, a second end, and a migration proof membrane separating the barrel into two chambers;

providing a substance in each chamber;

sealing the forward end of the barrel;

providing a slidable plunger in the second end of the barrel;

positioning a needle assembly in said receiving portion so as not to puncture the seal at the forward end;

providing a front cover over said barrel and needle assembly;

providing internal guide means in said cover for moving the membrane toward the plunger responsive to rotation of the cover;

storing the injector; and thereafter moving said membrane and plunger toward one another to rupture the membrane, by rotation the cover;

thereafter moving said needle assembly toward the barrel to puncture the seal; and thereafter moving said plunger towards the forward end of the barrel to discharge the contents of the barrel through the needle.

29. A method according to claim 28, comprising the step, in conjunction with moving the plunger forward, of moving the barrel and needle assembly forward to penetrate the front cover.

30. A method according to claim 29, wherein the step of causing the needle assembly to penetrate the seal is effected by pushing the barrel forward so that the needle engages the front cover and is pushed back through the seal.

* * * * *